(12) United States Patent
Lagodzki et al.

(10) Patent No.: US 9,662,120 B2
(45) Date of Patent: May 30, 2017

(54) DETACHABLE TREATMENT DEVICE DELIVERY SYSTEM UTILIZING COMPRESSION AT ATTACHMENT ZONE

(71) Applicant: Cook Medical Technologies LLC, Bloomington, IN (US)

(72) Inventors: Karol Lagodzki, Bloomington, IN (US); Jeremy Schaeffer, Bloomington, IN (US); Elizabeth Theobald, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 138 days.

(21) Appl. No.: 14/290,301

(22) Filed: May 29, 2014

(65) Prior Publication Data

US 2015/0057699 A1    Feb. 26, 2015

Related U.S. Application Data

(60) Provisional application No. 61/869,130, filed on Aug. 23, 2013.

(51) Int. Cl.
*A61M 29/00* (2006.01)
*A61B 17/12* (2006.01)

(52) U.S. Cl.
CPC .... *A61B 17/12113* (2013.01); *A61B 17/1214* (2013.01); *A61B 17/12022* (2013.01);
(Continued)

(58) Field of Classification Search
CPC ........ A61B 17/12022; A61B 17/12027; A61B 2017/1205; A61B 2017/12054;
(Continued)

(56) References Cited

U.S. PATENT DOCUMENTS 5,217,484 A    6/1993    Marks
5,261,916 A    11/1993   Engelson
(Continued)

FOREIGN PATENT DOCUMENTS

WO    9426175    11/1994

OTHER PUBLICATIONS

Sandeep Vaidya, M.D., Kathleen R. Tozer, M.D and Jarvis Chen, M.D.; An Overview of Embolic Agents; pp. 204-215.
(Continued)

*Primary Examiner* — Jonathan Miles
*Assistant Examiner* — Kendra Obu
(74) *Attorney, Agent, or Firm* — Liell & McNeil

(57) ABSTRACT

A detachable treatment device delivery system includes a delivery sheath defining a lumen, a treatment device having a proximal attachment segment configured for receipt within the delivery sheath, and a deployment wire configured for receipt within the delivery sheath. A delivery configuration is defined by an overlap of a distal segment of the deployment wire and the proximal attachment segment within an attachment zone of the delivery sheath. In the delivery configuration, an inner surface of the delivery sheath is outwardly expanded and compressed around the deployment wire and the treatment device at the overlap. In a deployed configuration, the deployment wire is proximally spaced from the attachment zone, and the proximal attachment segment is distally spaced from the attachment zone and the distal opening.

16 Claims, 1 Drawing Sheet

(52) U.S. Cl.
CPC . *A61B 17/12027* (2013.01); *A61B 2017/1205* (2013.01); *A61B 2017/12054* (2013.01)

(58) Field of Classification Search
CPC  A61B 2017/12077; A61B 2017/12081; A61B 2017/12095; A61B 17/12031; A61B 17/12036; A61B 17/1204; A61B 17/12045; A61B 17/12099; A61B 17/12109; A61B 17/12113; A61B 17/12131; A61B 17/1214; A61B 17/12145; A61B 17/12154; A61B 2017/12068; A61B 2017/12127
See application file for complete search history.

(56)  References Cited

U.S. PATENT DOCUMENTS

| | | |
|---|---|---|
| 5,263,964 A | 11/1993 | Purdy |
| 5,304,195 A | 4/1994 | Twyford, Jr. et al. |
| 5,405,379 A | 4/1995 | Lane |
| 5,417,708 A | 5/1995 | Hall et al. |
| 5,891,155 A | 4/1999 | Irie |
| 6,183,491 B1 | 2/2001 | Lulo |
| 6,773,448 B2 | 8/2004 | Kusleika et al. |
| 6,849,081 B2 | 2/2005 | Sepetka et al. |
| 7,118,539 B2 | 10/2006 | Vrba et al. |
| 7,344,553 B2 | 3/2008 | Opolski et al. |
| 7,371,251 B2 | 5/2008 | Mitelberg et al. |
| 7,618,435 B2 | 11/2009 | Opolski |
| 7,942,894 B2 | 5/2011 | West |
| 8,062,325 B2 | 11/2011 | Mitelberg et al. |
| 8,118,817 B2 | 2/2012 | Tekulve |
| 8,292,872 B2 | 10/2012 | Soetermans |
| 8,333,796 B2 | 12/2012 | Tompkins et al. |
| 2001/0002438 A1 | 5/2001 | Sepetka et al. |
| 2005/0107823 A1 | 5/2005 | Leone et al. |
| 2005/0149107 A1* | 7/2005 | Jones .............. A61B 17/12022 606/200 |
| 2005/0283182 A1* | 12/2005 | Pierce .............. A61B 17/12022 606/200 |
| 2006/0025801 A1 | 2/2006 | Lulo et al. |
| 2006/0025802 A1 | 2/2006 | Sowers |
| 2006/0025803 A1 | 2/2006 | Mitelberg et al. |
| 2006/0116709 A1 | 6/2006 | Sepetka et al. |
| 2006/0116714 A1* | 6/2006 | Sepetka .......... A61B 17/12022 606/200 |
| 2007/0179520 A1 | 8/2007 | West |
| 2007/0299422 A1* | 12/2007 | Inganas .............. A61B 17/0057 604/508 |
| 2008/0046092 A1* | 2/2008 | Davis .............. A61B 17/12022 623/23.72 |
| 2008/0097462 A1 | 4/2008 | Mitelberg et al. |
| 2008/0097508 A1* | 4/2008 | Jones .............. A61B 17/12022 606/191 |
| 2008/0114391 A1 | 5/2008 | Dieck et al. |
| 2008/0221654 A1 | 9/2008 | Buiser et al. |
| 2008/0228215 A1* | 9/2008 | Strauss .......... A61B 17/12022 606/191 |
| 2009/0270877 A1 | 10/2009 | Johnson et al. |
| 2009/0287291 A1 | 11/2009 | Becking et al. |
| 2012/0041472 A1 | 2/2012 | Tan et al. |
| 2012/0209310 A1 | 8/2012 | Chen et al. |
| 2012/0265237 A1 | 10/2012 | Evert |
| 2013/0072961 A1 | 3/2013 | Cage et al. |

OTHER PUBLICATIONS

Jorge E. Lopera, M.D., F.S.I.R.; Embolization in Trauma: Principles and Techniques; pp. 14-28.

* cited by examiner

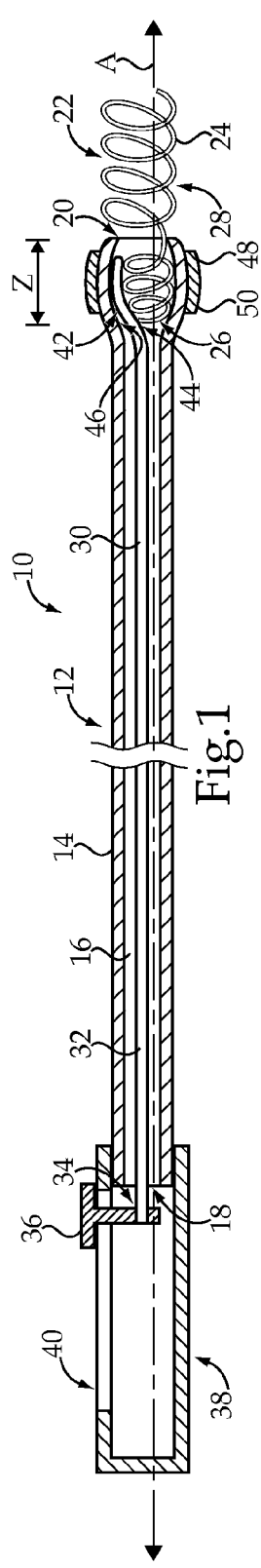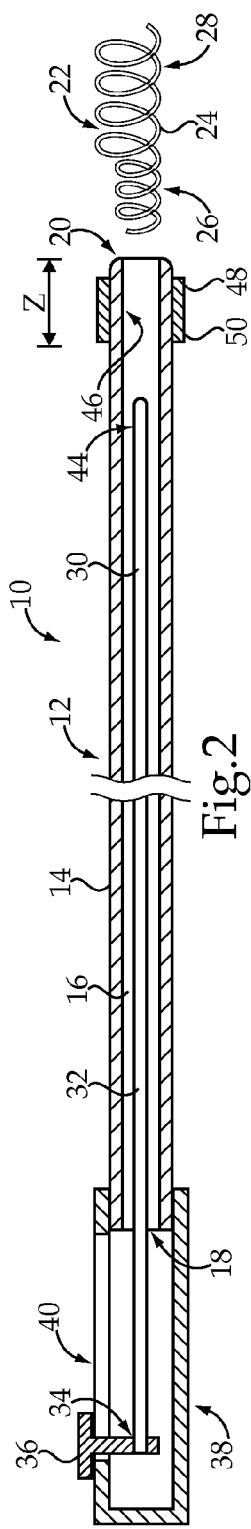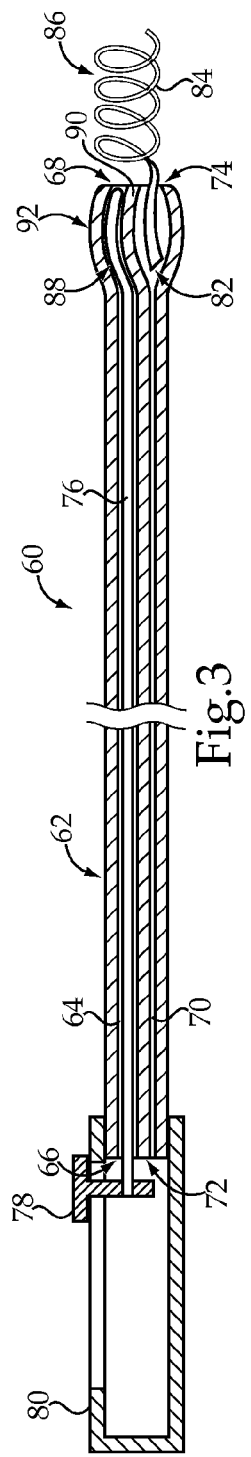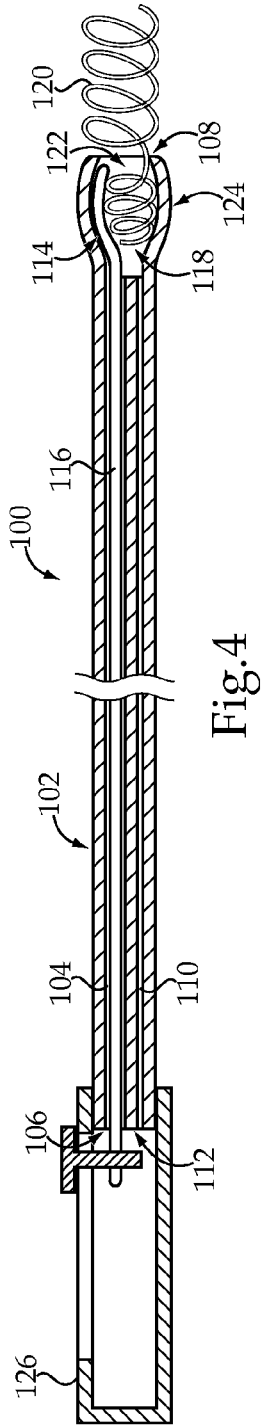

DETACHABLE TREATMENT DEVICE DELIVERY SYSTEM UTILIZING COMPRESSION AT ATTACHMENT ZONE

TECHNICAL FIELD

The present disclosure relates generally to a delivery system for detachable treatment devices, and more particularly to a delivery system for compressing an overlap of a deployment wire and a treatment device within an attachment zone of a delivery sheath.

BACKGROUND

Medical treatment devices, such as, for example, embolization coils, microcoils, and plugs, are used to restrict or block blood flow to arterio-venous malformations and other vascular lesions. For example, these treatment devices may be delivered into an aneurysm of a patient to prevent blood from entering the aneurysm. Embolization is typically a non-surgical, minimally invasive procedure that involves pushing or injecting the treatment devices, or, alternatively, detaching the treatment devices at the treatment site. Both delivery methods offer benefits and suffer drawbacks, particularly depending on the specifics of the procedure being performed.

According to one example, U.S. Pat. No. 6,183,491 to Lulo discloses an embolic coil deployment system with an improved embolic coil. The embolic coil deployment system includes a positioning catheter having a distal tip for retaining the embolic coil. When a hydraulic pressure is applied to an interior of the positioning catheter, the distal section of the positioning catheter expands radially to release the embolic coil. In order to prevent the proximal portion of the embolic coil from stretching or unwinding, a platinum support wire is welded to a proximal sealing plug, which serves to prevent the flow of fluid through the lumen of the embolic coil. Although the embolic coil deployment system of Lulo may be suitable for some applications, there is a continuing need for improved deployment systems, including those that offer control, reliability, simplicity, and the ability to navigate tortuous anatomy.

The present disclosure is directed toward one or more of the problems or issues set forth above.

SUMMARY OF THE DISCLOSURE

In one aspect, a detachable treatment device delivery system includes a delivery sheath defining a lumen extending from a proximal opening to a distal opening. A treatment device has a proximal attachment segment configured for receipt within the delivery sheath. The detachable treatment device delivery system also includes a deployment wire configured for receipt within the delivery sheath. A delivery configuration is defined by an overlap of a distal segment of the deployment wire and the proximal attachment segment of the treatment device along a longitudinal axis of the delivery sheath within an attachment zone defined by the delivery sheath. According to the delivery configuration, an inner surface of the delivery sheath defining the attachment zone is outwardly expanded and compressed around the deployment wire and the treatment device at the overlap. In a deployed configuration, the deployment wire is within the delivery sheath and is proximally spaced from the attachment zone, and the proximal attachment segment of the treatment device is distally spaced from the attachment zone and the distal opening.

In another aspect, a method of deploying a treatment device using a detachable treatment device delivery system is provided. The detachable treatment device delivery system includes a delivery sheath defining a lumen extending from a proximal opening to a distal opening, and a deployment wire. The method includes compressing an overlap of a distal segment of the deployment wire and a proximal attachment segment of the treatment device within an attachment zone defined by the delivery sheath using the delivery sheath. An inner surface of the delivery sheath is outwardly expanded at the overlap responsive to the compressing step. The method also includes proximally retracting the deployment wire within the delivery sheath such that the deployment wire is proximally spaced from the attachment zone, and releasing the treatment device from the delivery sheath through the distal opening responsive to the proximally retracting step such that the proximal attachment segment of the treatment device is distally spaced from the attachment zone and the distal opening.

BRIEF DESCRIPTION OF THE DRAWINGS

FIG. 1 is a partially sectioned side diagrammatic view of a detachable treatment device delivery system, shown in a delivery configuration, according to one embodiment of the present disclosure;

FIG. 2 is a partially sectioned side diagrammatic view of the detachable treatment device delivery system of FIG. 1, shown in a deployed configuration;

FIG. 3 is a partially sectioned side diagrammatic view of a detachable treatment device delivery system, according to another embodiment of the present disclosure; and FIG. 4 is a partially sectioned side diagrammatic view of a detachable treatment device delivery system, according to another embodiment of the present disclosure.

DETAILED DESCRIPTION

Referring to FIG. 1, there is shown a detachable treatment device delivery system 10 according to one embodiment of the present disclosure. Although not shown, the detachable treatment device delivery system 10 may be provided within a sterile, tear open package, as is known in the art. In performing an embolization procedure on a patient, some or all of the components of the detachable treatment device delivery system 10 may be used, depending upon the specifics of the procedure to be performed. As should be appreciated, however, the components shown in FIG. 1 might be separately packaged and/or the detachable treatment device delivery system 10 might also include components in addition to those shown, including components routinely used in percutaneous vascular procedures.

The detachable treatment device delivery system 10 includes a delivery sheath 12 having an elongate tubular body 14 defining a lumen 16 extending from a proximal opening 18 to a distal opening 20. In the present disclosure, "proximal" will be used to refer to the end of a component or feature that is closest to a clinician, while "distal" is used to refer to a component or feature that is farthest away from the clinician. Such meanings are consistent with conventional use of the terms and, as such, should be understood by those skilled in the art.

The elongate tubular body 14 may be made from any common medical tube material, such as, for example, polytetrafluoroethylene (PTFE), high density polyethylene (HDPE), nylon, polyetheretherketone (PEEK), or any vinyl, plastic, rubber, silicone, or metal and may exhibit both stiffness, or firmness, and flexibility. Materials as well as dimensions may vary depending on the particular application. However, it may be desirable to dimension the delivery sheath 12 for receipt within a particular catheter or microcatheter. For example, the delivery sheath 12 may have an outer diameter, according to all potential configurations, that is less than 0.035 inch, or other selected catheter inner diameter. A length of the delivery sheath 12 may be between about 50 centimeters to about 225 centimeters, which may correspond substantially to a delivery catheter with which the detachable treatment device delivery system 10 is to be used.

A treatment device 22, which may, for example, be an embolization coil 24, has a proximal attachment segment 26 configured for receipt within the delivery sheath 12. According to a delivery configuration, as shown in FIG. 1, the proximal attachment segment 26 may be disposed within the lumen 16 of the delivery sheath 12, while a distal end 28 of the treatment device 22 is distally disposed relative to the distal opening 20 of the delivery sheath 12. As is known to those skilled in the art, the embolization coil 24 may have a preformed coiled shape. According to the exemplary embodiment of FIG. 1, both the proximal attachment segment 26 and the distal end 28 may conform to the preformed coiled shape. However, one or both of the proximal attachment segment 26 and the distal end 28 may be urged against the preformed coiled shape that is shown. Although the shapes and sizes of coils may vary greatly, it should be appreciated that the embolization coil 24 may have an outer diameter, according to the preformed coil shape, between about 0.005 and 0.05 inch and may have a length of between about 1.5 to 30 centimeters.

Although treatment device 22 is exemplified as an embolization coil, it should be appreciated that various other treatment devices, including plugs, may be used with the detachable treatment device delivery system 10 instead of the embolization coil 24. To accommodate use with the detachable treatment device delivery system 10, the treatment device 22 preferably includes the proximal attachment segment 26, which is configured for receipt within the delivery sheath 12. In particular, the proximal attachment segment 26 should be sized and shaped for receipt within the delivery sheath 12 and configured for detachable retention within the delivery sheath 12 as described herein. The proximal attachment segment 26 may be integral with the distal end 28, or the proximal attachment segment 26 and the distal end 28 may be separate components that are attached together using known attachment means.

The detachable treatment device delivery system 10 also includes a deployment wire 30 configured for receipt within the delivery sheath 12. The deployment wire 30 may have an elongate body 32 made from any of a variety of medical grade materials, including those identified with respect to the delivery sheath 12. As shown in the delivery configuration of FIG. 1, the deployment wire 30 may be disposed within the lumen 16 of the delivery sheath 12 and movable along a longitudinal axis A of the delivery sheath 12. In particular, for example, a proximal end 34 may be attached to, or configured to move with, a movable portion 36 of a handle 38. The handle 38 may be disposed over the proximal opening 18 of the delivery sheath 12 and may include an elongate slot 40 within which the movable portion 36 may be retracted. Although a simplified version of handle 38 is shown, it should be appreciated that a variety of handles, ranging in complexity, may be adapted for use with the detachable treatment device delivery system 10.

The delivery configuration of FIG. 1 is defined by an overlap, shown at 42, of a distal segment 44 of the deployment wire 30 and the proximal attachment segment 26 of the treatment device 22 along the longitudinal axis A. The overlap 42 is positioned within an attachment zone Z defined by the delivery sheath 12. The attachment zone Z may have a length corresponding to, or including, portions of the deployment wire 30 and the treatment device 22 that are overlapped. Also according to the delivery configuration, an inner surface 46 of the delivery sheath 12 defining the attachment zone Z is outwardly, or radially, expanded and compressed around the deployment wire 30 and the treatment device 22 at the overlap 42.

According to embodiments in which the delivery sheath 12 defines a single lumen 16, such as the embodiment of FIG. 1, the distal segment 44 of the deployment wire 30 and the proximal attachment segment 26 of the treatment device 22 may be in direct contact in the delivery configuration. As such, an outer diameter of the proximal attachment segment 26 of the treatment device 22 and the distal segment 44 of the deployment wire 30 may define a combined diameter that is slightly larger, or greater, than an inner diameter of the delivery sheath 12. The delivery sheath 12, at the attachment zone Z, may be sufficiently compliant to radially expand as the inner surface 46 compresses the deployment wire 30 and the treatment device 22 into a releasable, or detachable, engagement. The distal segment 44 of the deployment wire 30 may also be sufficiently compliant to adapt to the compression in the delivery configuration.

According to some embodiments, a compressive band 48 may be positioned over the delivery sheath 12 at the attachment zone Z. The compressive band 48 may assist in providing a compressive force to maintain the releasable engagement of the deployment wire 30 and the treatment device 22 at the overlap 42. The compressive band 48 may be, or may include, a radiopaque marker 50 to facilitate fluoroscopic visualization of the attachment zone Z. Additional or alternative radiopaque markings may be provided on components of the detachable treatment device delivery system 10, including radiopaque markings on portions of the deployment wire 30 and/or treatment device 22.

The handle 38 may be manipulated to move the detachable treatment device delivery system 10 from the delivery configuration of FIG. 1 to a deployed configuration, as shown in FIG. 2. In particular, the movable portion 36 of the handle 38 may be proximally retracted to correspondingly retract the deployment wire 30. According to the deployment configuration, the deployment wire 30 is proximally spaced from the attachment zone Z, and the proximal attachment segment 26 of the treatment device 22 is distally spaced from the attachment zone Z and the distal opening 20. That is, once the deployment wire 30 is retracted such that the distal segment 44 of the deployment wire 30 and the proximal attachment segment 26 of the treatment device 22 are no longer overlapped, the proximal attachment segment 26 of the treatment device 22 is permitted to advance through the distal opening 20.

According to an alternative embodiment, as shown in FIG. 3, a detachable treatment device delivery system 60 according to the present disclosure may include a dual lumen sheath 62. That is, the delivery sheath 62 may define a first lumen 64 extending from a first proximal opening 66 to a first distal opening 68, and a second lumen 70 extending from a second proximal opening 72 to a second distal opening 74. The lumens 64 and 70 may be arranged in various configurations, including a side-by-side configuration or a coaxial configuration. A deployment wire 76 may be attached to a movable portion 78 of a proximal handle 80 and may be movable within the first lumen 64. A proximal attachment segment 82 of a treatment device 84 may be disposed through the second distal opening 74 and within the second lumen 70.

The proximal attachment segment 82, which may be integral with or a separate component from a distal end 86 of the treatment device 84, may be urged against a preformed coiled shape in a delivery configuration, as shown. Alternatively, the proximal attachment segment 82 may have a preformed straightened shape that remains straightened after the treatment device 84 has been deployed. According to the embodiment of FIG. 3, a distal segment 88 of the deployment wire 76 and the proximal attachment segment 82 of the treatment device 84 may be in indirect contact through a wall 90 separating the first and second lumens 64 and 70 at an overlap 92.

The first and second lumens 64 and 70, along with the distal segment 88 of the deployment wire 76 and the proximal attachment segment 82 of the treatment device 84, may be sized such that the combined diameter of the deployment wire 76, the treatment device 84, and the wall 90 are great enough to radially expand the delivery sheath 62 at the overlap 92 as the deployment wire 76 and treatment device 84 are compressed together in a releasable engagement.

Turning now to FIG. 4, another alternative embodiment is shown. In particular, a detachable treatment device delivery system 100 may include a delivery sheath 102 defining a first lumen 104 extending from a first proximal opening 106 to an open distal end 108, and a second lumen 110 extending from a second proximal opening 112 to the open distal end 108. In a delivery configuration, as shown, a distal segment 114 of a deployment wire 116 and a proximal attachment segment 118 of a treatment device 120 may be in direct contact in a common area 122 of the delivery sheath 102 that is proximally spaced from the open distal end 108. In particular, the deployment wire 116 and the treatment device 120 may define an overlap 124 within the common area 122. At the overlap 124, the delivery sheath 102 is outwardly, or radially, expanded and compressed around the distal segment 114 of the deployment wire 116 and the proximal attachment segment 118 of the treatment device 120. To release the treatment device 120 completely from the delivery sheath 102, the deployment wire 116 may be proximally refracted using a handle 126.

INDUSTRIAL APPLICABILITY

Referring generally to FIGS. 1-4 and more specifically to the embodiment of FIGS. 1 and 2, a method of deploying the treatment device 22 using the detachable treatment device delivery system 10 will be described. To load the detachable treatment device delivery system 10 and place the same in a delivery configuration, the proximal attachment segment 26 of the treatment device 22 may be inserted through the distal opening 20 of the delivery sheath 12. As stated above, the components are sized and/or configured such that when the proximal attachment segment 26 of the treatment device 22 and the distal segment 44 of the deployment wire 30 are positioned within the delivery sheath 12 to define the overlap 42, the inner surface 46 of the delivery sheath 12 is outwardly expanded and compressed around the proximal attachment segment 26 of the treatment device 22 and the distal segment 44 of the deployment wire 30.

Those skilled in the art should appreciate that the detachable treatment device delivery system 10 may be provided in the preloaded state described above and may also include a delivery cannula for maintaining a straightened configuration of the distal end 28 of the treatment device 22 during delivery. The delivery cannula may be configured to retract during advancement of the detachable treatment device delivery system 10 through a delivery catheter. The delivery catheter, according to one example, may then maintain a straightened configuration of the distal end 28 of the treatment device 22 as the detachable treatment device delivery system 10 is advanced, in the delivery configuration, to a treatment site within a patient site, such as, for example, a vascular structure.

When the detachable treatment device delivery system 10 is properly positioned, the handle 38 may be manipulated to proximally retract the deployment wire 30 within the delivery sheath 12 such that the deployment wire 30 is proximally spaced from the attachment zone Z. As such, the treatment device 22 may be released from the delivery sheath 12 through the distal opening 20 in response to the retraction of the deployment wire 30 such that the proximal attachment segment 26 of the treatment device 22 is distally spaced from the attachment zone Z and the distal opening 20.

It should be appreciated that testing may be conducted to determine a desired amount of compression to provide the releasable engagement of the treatment device 22. In particular, it may be desired to provide sufficient compression to reliably retain the treatment device 22 in an attached configured as the detachable treatment device delivery system 10 navigates tortuous anatomy and is moved both proximally and distally. However, if too much compression is provided, it might be difficult to retract the deployment wire 30 and/or retraction of the deployment wire 30 may undesirably retract the proximal attachment segment 26 of the treatment device 22. According to some embodiments, the compressive band 48 may be helpful in arriving at a desired level of compression. The detachable treatment device delivery system 10 may provide a low profile mechanism for providing control and reliable detachment of the treatment device 22 at a treatment site.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A detachable treatment device delivery system, comprising:
    a delivery sheath defining a lumen extending from a proximal opening to a distal opening;
    a treatment device having a proximal attachment segment, which has a preformed coil shape, received within the delivery sheath in a delivery configuration; and
    a deployment wire configured for receipt within the delivery sheath;
    the delivery configuration defined by an overlap of a distal segment of the deployment wire and the preformed coil shape of the proximal attachment segment of the treatment device along a longitudinal axis of the delivery sheath within an attachment zone defined by the delivery sheath, wherein an inner surface of the delivery sheath defining the attachment zone is radially outwardly expanded and compressed around the deployment wire and the treatment device at the overlap;
    a deployed configuration in which the deployment wire is within the delivery sheath and is proximally spaced from the attachment zone, and the proximal attachment segment of the treatment device is distally spaced from the attachment zone and the distal opening.

2. The detachable treatment device delivery system of claim 1, wherein:
the delivery sheath defines a single lumen; and
the distal segment of the deployment wire and the proximal attachment segment of the treatment device are in direct contact in the delivery configuration.

3. The detachable treatment device delivery system of claim 1, wherein:
the delivery sheath defines a first lumen extending from a first proximal opening to a first distal opening and a second lumen extending from a second proximal opening to a second distal opening; and
in the delivery configuration, the distal segment of the deployment wire and the proximal attachment segment of the treatment device are in indirect contact through a wall separating the first and second lumens.

4. The detachable treatment device delivery system of claim 1, wherein:
the delivery sheath defines a first lumen extending from a first proximal opening to an open distal end and a second lumen extending from a second proximal opening to the open distal end; and
in the delivery configuration, the distal segment of the deployment wire and the proximal attachment segment of the treatment device are in direct contact in a common area of the delivery sheath that is proximally spaced from the open distal end.

5. The detachable treatment device delivery system of claim 1, further including a compressive band positioned over the delivery sheath at the attachment zone.

6. The detachable treatment device delivery system of claim 5, wherein the compressive band includes a radiopaque marker.

7. The detachable treatment device delivery system of claim 1, wherein, in the deployed configuration, a distal end of the treatment device conforms to a preformed coiled shape.

8. The detachable treatment device delivery system of claim 7, wherein, in the delivery configuration, the preformed coiled shape of the proximal attachment segment of the treatment device is compressed against the delivery sheath.

9. The detachable treatment device delivery system of claim 1, further including a radiopaque marker attached to the delivery sheath at the attachment zone.

10. The detachable treatment device delivery system of claim 1, further including a handle disposed over the proximal opening of the delivery sheath and configured to move the detachable treatment device delivery system from the delivery configuration to the deployed configuration.

11. A method of deploying a treatment device using a detachable treatment device delivery system, the detachable treatment device delivery system including a delivery sheath defining a lumen extending from a proximal opening to a distal opening, a treatment device having a proximal attachment segment, which has a preformed coil shape, received within the delivery sheath in a delivery configuration, and a deployment wire configured for receipt within the delivery sheath, and the delivery configuration being defined by an overlap of a distal segment of the deployment wire and the preformed coil shape of the proximal attachment segment of the treatment device along a longitudinal axis of the delivery sheath within an attachment zone defined by the delivery sheath, wherein an inner surface of the delivery sheath defining the attachment zone is radially outwardly expanded and compressed around the deployment wire and the treatment device at the overlap; a deployed configuration in which the deployment wire is within the delivery sheath and is proximally spaced from the attachment zone, and the proximal attachment segment of the treatment device is distally spaced from the attachment zone and the distal opening, the method comprising steps of:
compressing the overlap of the distal segment of the deployment wire and the preformed coil shape of the proximal attachment segment of the treatment device within the attachment zone defined by the delivery sheath using the delivery sheath;
outwardly expanding the inner surface of the delivery sheath at the overlap responsive to the compressing step;
proximally retracting the deployment wire within the delivery sheath such that the deployment wire is proximally spaced from the attachment zone; and
releasing the treatment device from the delivery sheath through the distal opening responsive to the proximally retracting step such that the proximal attachment segment of the treatment device is distally spaced from the attachment zone and the distal opening.

12. The method of claim 11, wherein the compressing step includes directly contacting the distal segment of the deployment wire and the proximal attachment segment of the treatment device in the delivery sheath.

13. The method of claim 11, wherein the compressing step includes indirectly contacting the distal segment of the deployment wire and the proximal attachment segment of the treatment device through a wall separating a first lumen and a second lumen defined by the delivery sheath.

14. The method of claim 11, wherein the compressing step includes the delivery sheath using a compressive band positioned over the delivery sheath at the attachment zone.

15. The method of claim 11, wherein the step of releasing the treatment device from the delivery sheath includes conforming a distal end of the treatment device to a preformed coiled shape.

16. The method of claim 11, further including manipulating a handle disposed over the proximal opening of the delivery sheath to proximally retract the deployment wire.

* * * * *